US008942439B2

(12) United States Patent
Monden

(10) Patent No.: US 8,942,439 B2
(45) Date of Patent: Jan. 27, 2015

(54) FINGERPRINT AUTHENTICATION SYSTEM, FINGERPRINT AUTHENTICATION METHOD, AND FINGERPRINT AUTHENTICATION PROGRAM

(75) Inventor: Akira Monden, Minato-ku (JP)

(73) Assignee: NEC Corporation, Tokyo (JP)

( * ) Notice: Subject to any disclaimer, the term of this patent is extended or adjusted under 35 U.S.C. 154(b) by 123 days.

(21) Appl. No.: 13/696,518

(22) PCT Filed: May 18, 2011

(86) PCT No.: PCT/JP2011/061402
§ 371 (c)(1),
(2), (4) Date: Nov. 6, 2012

(87) PCT Pub. No.: WO2011/152213
PCT Pub. Date: Dec. 8, 2011

(65) Prior Publication Data
US 2013/0051638 A1   Feb. 28, 2013

(30) Foreign Application Priority Data
Jun. 4, 2010   (JP) .................................. 2010-129059

(51) Int. Cl.
*G06K 9/36*   (2006.01)
*G05B 19/00*   (2006.01)
(Continued)

(52) U.S. Cl.
CPC ............ *A61B 5/1172* (2013.01); *G06K 9/0008* (2013.01)
USPC ............ 382/125; 382/195; 340/5.8; 340/5.53

(58) Field of Classification Search
USPC ........ 340/5.53, 5.83, 5.52, 5.2, 5.1, 5.8, 5.81, 340/5.82, 5.51; 356/71; 713/186; 382/125, 382/195, 100, 115, 124, 126, 181, 209, 190, 382/224, 217, 218, 254, 260, 199, 168, 170, 382/256, 258, 266, 275, 107, 276, 278
See application file for complete search history.

(56) References Cited

U.S. PATENT DOCUMENTS 7,274,808 B2 *   9/2007   Baharav et al. ............... 382/124
7,359,782 B2 *   4/2008   Breed ............................ 701/45
(Continued)

FOREIGN PATENT DOCUMENTS

JP   2739856 B2   4/1997
JP   9-134419 A   5/1997
(Continued)

*Primary Examiner* — Sheela Chawan
(74) *Attorney, Agent, or Firm* — Sughrue Mion, PLLC

(57) ABSTRACT

To improve the precision with which a false finger formed by attaching a transparent thin film to a surface of a finger is identified, a fingerprint authentication system includes: an image division unit 31 that divides a captured image of an authentication subject to be subjected to fingerprint authentication into a plurality of small regions; a frequency analysis unit 32 that performs a frequency analysis on each of the small regions; a ridge candidate extraction unit 33 that extracts frequency components corresponding to ridge candidates in the small regions from frequency components obtained in the frequency analysis; a continuous ridge candidate group generation unit 34 that compares the ridge candidates between adjacent small regions, and when the ridge candidates satisfy a condition enabling the ridge candidates to be determined continuous, generates a continuous ridge candidate group including the ridge candidates; and a determination unit 35 that determines that an abnormality exists in the image when overlap exists between the image regions corresponding to the continuous ridge candidate group.

9 Claims, 16 Drawing Sheets

(51) Int. Cl.
 *G06K 9/00* (2006.01)
 *A61B 5/117* (2006.01)

(56) References Cited

U.S. PATENT DOCUMENTS

| | | | |
|---|---|---|---|
| 7,394,918 B2 * | 7/2008 | Mihara et al. | 382/107 |
| 8,131,026 B2 * | 3/2012 | Benkley et al. | 382/124 |
| 8,195,005 B2 * | 6/2012 | Huang | 382/284 |
| 8,224,064 B1 * | 7/2012 | Hassebrook et al. | 382/154 |
| 2006/0023921 A1 * | 2/2006 | Saitoh et al. | 382/115 |
| 2007/0189586 A1 | 8/2007 | Monden | |

FOREIGN PATENT DOCUMENTS

| | | |
|---|---|---|
| JP | 2637253 B2 | 8/1997 |
| JP | 2003-050993 A | 2/2003 |
| JP | 2005-204681 A | 8/2005 |
| JP | 2007-249296 A | 9/2007 |
| JP | 2008-006146 A | 1/2008 |
| JP | 2010-282519 A | 12/2010 |
| WO | 2005/086091 A1 | 9/2005 |
| WO | 2011/058836 A1 | 5/2011 |
| WO | 2011/058837 A1 | 5/2011 |

* cited by examiner

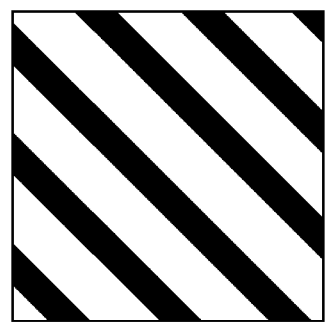
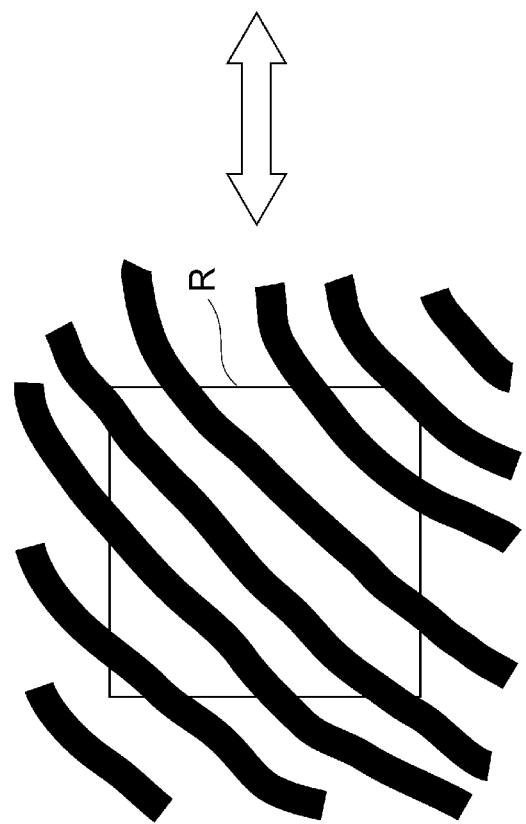

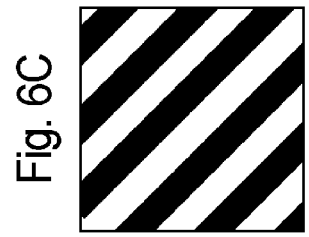
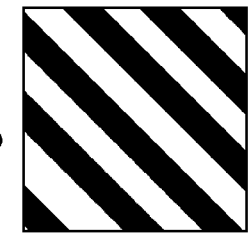
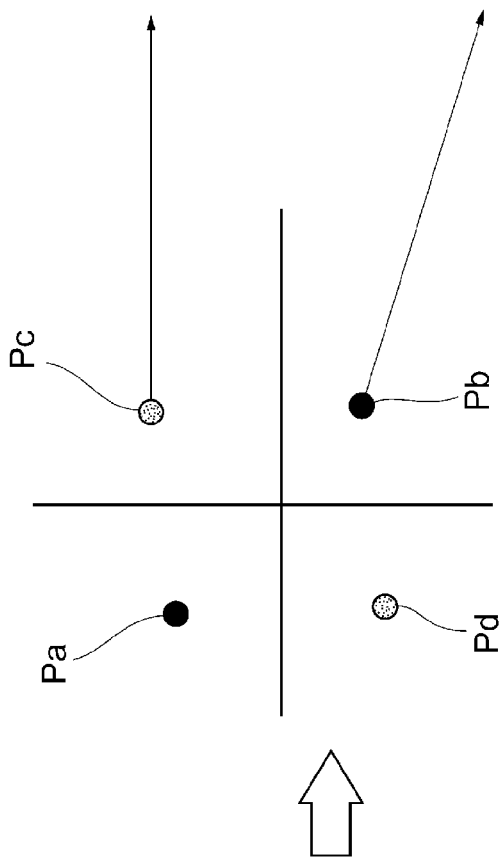
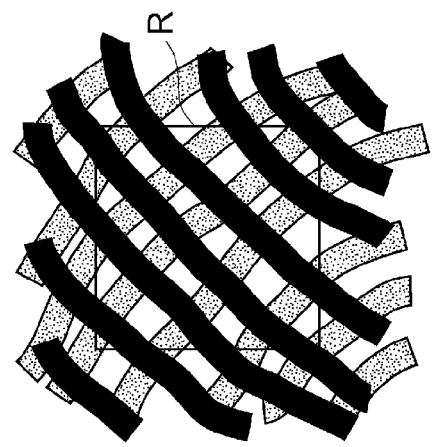

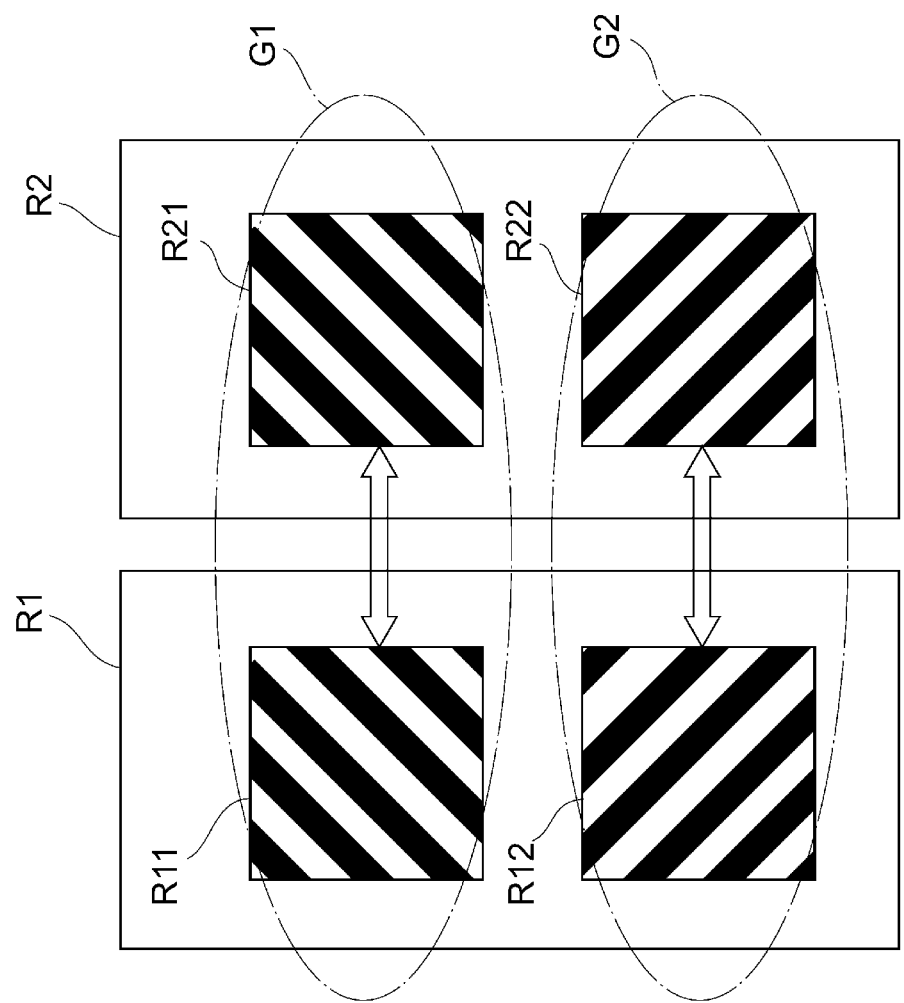

FINGERPRINT AUTHENTICATION SYSTEM, FINGERPRINT AUTHENTICATION METHOD, AND FINGERPRINT AUTHENTICATION PROGRAM

CROSS REFERENCE TO RELATED APPLICATIONS

This application is a National Stage of International Application No. PCT/JP2011/061402 filed May 18, 2011, claiming priority based on Japanese Patent Application No. 2010-129059, filed Jun. 4, 2010, the contents of all of which are incorporated herein by reference in their entirety.

BACKGROUND

The present invention relates to a fingerprint authentication system, a fingerprint authentication method, and a fingerprint authentication program.

In recent years, fingerprint authentication has gained attention as an authentication method for recognizing individuals. Fingerprints differ from person to person and do not vary over time. Accordingly, fingerprint authentication is more reliable than currently widespread password authentication and so on. With fingerprint authentication, however, it is necessary to prevent fraudulent behavior whereby the fingerprint of another individual is taken and the individual is impersonated using a forged false finger or the like. Following Patent Documents 1 and 2, for example, disclose a technique for preventing this fraudulent behavior by detecting a false finger using a color of a surface of the finger when irradiated with light as a reference. Further, in Patent Document 3, a false finger is detected by irradiating a finger with light from above and capturing an image of light transmitted through the interior of the finger. Furthermore, in Patent Document 4, light is emitted from a side of a finger, and a diffusion pattern of light transmitted through the interior of the finger is used to detect a false finger formed by attaching a thin film having a forged fingerprint thereon to the surface of the finger.

Moreover, a technique of extracting lines known as ridges in order to compare fingerprints exists. In Patent Document 5, for example, a ridge can be extracted with stability even when a fingerprint includes wrinkles and noise by performing frequency analysis in respective local regions, selecting ridge candidates in the form of peaks within a frequency space, and determining a ridge (a peak) from a continuity of the ridge.

Patent Document 1: Patent Publication JP-A-2003-50993
Patent Document 2: Japanese Patent Publication No. 2637253
Patent Document 3: Patent Publication JP-A-9-134419
Patent Document 4: Patent Publication JP-A-2007-249296
Patent Document 5: Japanese Patent Publication No. 2739856

With the technique described in Patent Documents 1 and 2, in which a false finger is detected using the color of the surface of the finger as a reference, and the technique described in Patent Document 3, in which a false finger is detected by irradiating a finger with light from above, a false finger formed by attaching a transparent thin film having a copy or the like of a fingerprint of another individual thereon to the surface of a finger cannot be detected. The reason for this is that with Patent Documents 1 and 2 it is difficult to differentiate between the color of the surface of the false finger to which the transparent thin film is attached and the color of skin, while with Patent Document 3, an attenuation factor of the light transmitted through the transparent thing film is low, making it difficult to differentiate between the light transmitted through the interior of the finger and the thin film and the light transmitted only through the interior of the finger.

With the technique described in Patent Document 4, in which a false finger is detected by irradiating a finger with light from a side, the light may not be emitted directly onto the transparent thin film attached to the surface of the finger, and in this case, the false finger cannot be detected, similarly to Patent Document 3. For example, when the finger is pressed against a fingerprint sensor surface, a part of the finger may cover a periphery of the thin film such that the light to be emitted onto the thin film is blocked by this part of the finger. In this case, the light is not emitted directly onto the thin film, and therefore a similar condition to that of Patent Document 3 occurs. In this condition, it is difficult to differentiate between the light transmitted through the interior of the finger and the thin film and the light transmitted only through the interior of the finger.

SUMMARY

The present invention has been designed to solve the problems described above, and an object thereof is to provide a fingerprint authentication system, a fingerprint authentication method, and a fingerprint authentication program with which an improvement can be achieved in the precision with which a false finger formed by attaching a transparent (including translucent; likewise hereafter) thin film to a surface of a finger is identified.

A fingerprint authentication system according to the present invention includes: an image division unit that divides a captured image of an authentication subject to be subjected to fingerprint authentication into a plurality of small regions; a frequency analysis unit that performs a frequency analysis on each of the small regions; a ridge candidate extraction unit that extracts frequency components corresponding to ridge candidates in the small regions from frequency components obtained in the frequency analysis; a continuous ridge candidate group generation unit that compares the ridge candidates between adjacent small regions, and when the ridge candidates satisfy a condition enabling the ridge candidates to be determined continuous, generates a continuous ridge candidate group including the ridge candidates; and a determination unit that determines that an abnormality exists in the image when overlap exists between the image regions corresponding to the continuous ridge candidate group.

A fingerprint authentication method according to the present invention includes the steps of: dividing a captured image of an authentication subject to be subjected to fingerprint authentication into a plurality of small regions; performing a frequency analysis on each of the small regions; extracting frequency components corresponding to ridge candidates in the small regions from frequency components obtained in the frequency analysis; comparing the ridge candidates between adjacent small regions, and when the ridge candidates satisfy a condition enabling the ridge candidates to be determined continuous, generating a continuous ridge candidate group including the ridge candidates; and determining that an abnormality exists in the image when overlap exists between the image regions corresponding to the continuous ridge candidate group.

A fingerprint authentication program according to the present invention causes a computer to execute the respective steps included in the fingerprint authentication method described above.

According to the present invention, a false finger formed by attaching a transparent thin film to a surface of a finger can be identified.

DESCRIPTION OF THE DRAWINGS

FIG. 4 is a view showing a relationship between a ridge pattern of a fingerprint and a two-dimensional sine wave;

FIG. 6 is a view showing the frequency space of a region in which a transparent thin film is adhered to a finger surface;

FIG. 7 is a view illustrating an example of generation of a continuous ridge candidate group;

DETAILED DESCRIPTION

A captured image of a finger surface having a fingerprint typically includes a pattern constituted by fingerprint ridges as well as wrinkles, noise, and so on. Therefore, to perform fingerprint authentication on the basis of this type of image, ridges alone are extracted from the captured image using a method such as that described above in Patent Document 5, for example, and compared with registered patterns.

Figure 16:
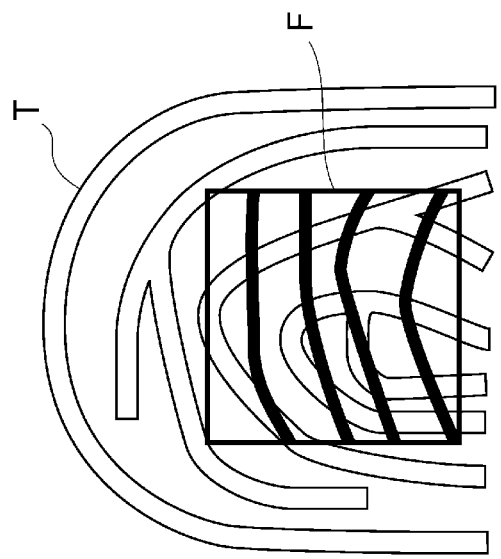
FIG. 16 is a view showing a condition in which a transparent thin film is adhered to a finger surface.

Incidentally, as shown in FIG. 16, when a transparent thin film having a forged fingerprint of another individual thereon is adhered to a surface of a finger, a condition in which a print pattern of a skin surface T and a print pattern of a thin film F are superimposed is portrayed on the captured image. In this case, the thin film is positioned on the surface of the skin, and therefore the print pattern on the thin film is depicted more thickly than the print pattern on the skin surface. Hence, when ridges are extracted using a typical method such as that described in Patent Document 5, for example, the print pattern on the thin film may be extracted as ridges in the part to which the thin film is adhered, and as a result, a fraudulent act of impersonating another individual may be performed. The present invention prevents fraudulent behavior using a false finger by determining whether or not this type of transparent thin film exists on the surface of a finger.

Preferred embodiments of a fingerprint authentication system, a fingerprint authentication method, and a fingerprint authentication program according to the present invention will be described below with reference to the attached drawings.

First Embodiment

Figure 1:
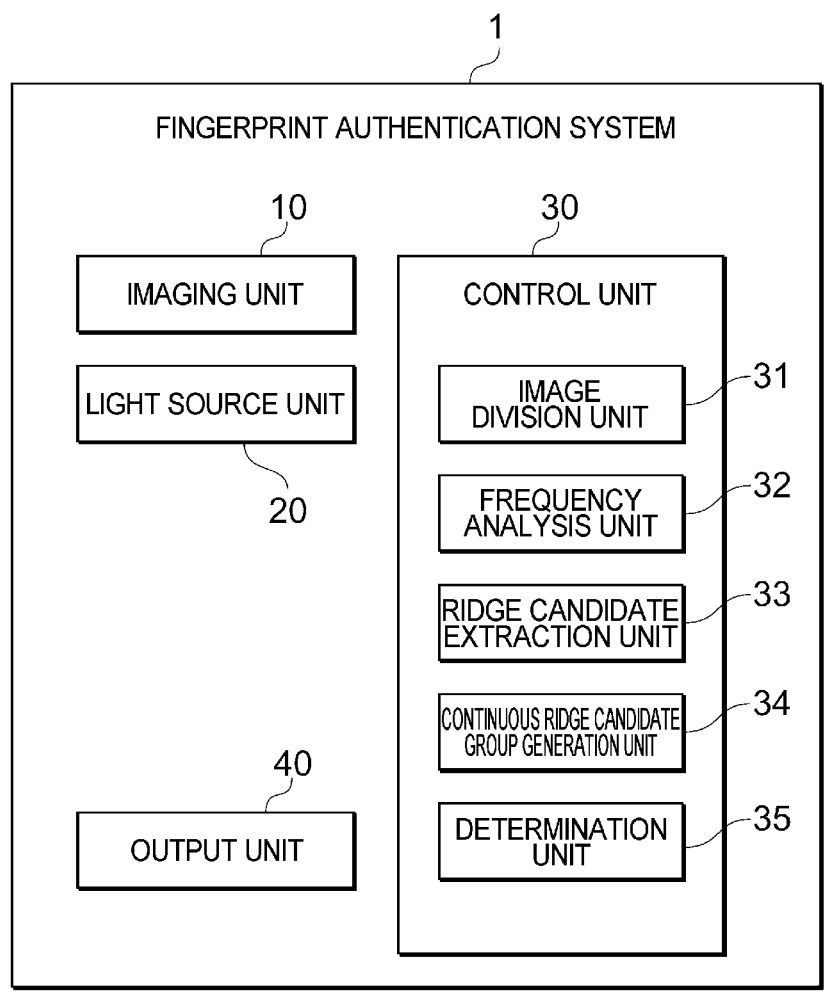
FIG. 1 is a block diagram showing a schematic configuration of a fingerprint authentication system according to a first embodiment.

First, referring to FIG. 1, an outline of the configuration of the fingerprint authentication system according to the first embodiment will be described. FIG. 1 is a block diagram showing the configuration of the fingerprint authentication system according to the first embodiment. A fingerprint authentication system 1 according to the first embodiment is applied to a biometric authentication system for authenticating a registrant using a fingerprint.

As shown in FIG. 1, the fingerprint authentication system 1 includes an imaging unit 10, a light source unit 20, a control unit 30, and an output unit 40. The imaging unit 10 is a CCD (Charge Coupled Device) camera, for example, which captures an image of an authentication subject placed in a predetermined placement region. The placement region may be provided on an upper surface of the fingerprint authentication system 1, for example. When a finger is placed in the placement region, the imaging unit 10 is disposed in a position where an image of a finger surface on which a fingerprint exists can be captured.

The light source unit 20 is an LED (Light-Emitting Diode), for example, which emits light onto the authentication subject during image capture of the authentication subject by the imaging unit 10. In this embodiment, the imaging unit 10 and the light source unit 20 together constitute a fingerprint sensor. An arrangement of the light source unit 20, the imaging unit 10, and the placement region is designed within a range enabling the imaging unit 10 to capture an image of the light from the light source unit 20 when reflected by the finger surface.

The control unit 30 controls the entire fingerprint authentication system 1 by executing various types of control processing. The output unit 40 is a warning lamp, for example, that is illuminated when the control unit 30 determines that the authentication subject is a false finger.

Note that the respective constituent elements of the fingerprint authentication system 1, i.e. the imaging unit 10, the light source unit 20, the control unit 30, and the output unit 40, are in principle identical to an imaging unit, a light source unit, a control unit, and an output unit of a conventional fingerprint authentication system. However, the fingerprint authentication system 1 differs from a conventional fingerprint authentication device in that the control unit 30 includes various functions for identifying a false finger.

Further, the fingerprint authentication system 1 physically includes a CPU (Central Processing Unit), a memory, the imaging unit, the light source unit, and the output unit. The memory includes, for example, a ROM (Read Only Memory) that stores programs and data processed by the CPU, and a RAM (Random Access Memory) mainly used as various working areas for the control processing. These elements are connected to each other via a bus. Functions of respective parts of the fingerprint authentication system 1 to be described below can be realized by having the CPU execute the programs stored in the ROM and perform processing using image data captured by the imaging unit and various data expanded in the RAM.

The control unit 30 includes, for example, an image division unit 31, a frequency analysis unit 32, a ridge candidate extraction unit 33, a continuous ridge candidate group generation unit 34, and a determination unit 35.

Figure 2:
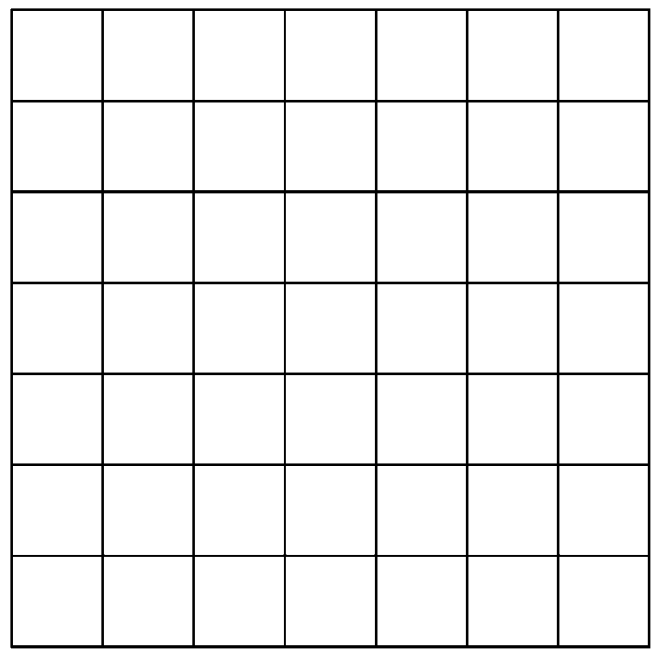
FIG. 2 is a view showing a condition in which an input image is divided into a lattice shape.

The image division unit 31 uses an image captured by the imaging unit 10 as an input image, and divides the input image into a plurality of small regions. As a division method, the input image may be divided into a lattice form such as that shown in FIG. 2, for example, so that the small regions do not overlap. Fingerprint ridges are not rectilinear, and therefore, when the small regions are too large, it becomes difficult to evaluate a continuity of a ridge between adjacent small regions, as will be described below. Hence, the small regions are preferably divided such that the fingerprint ridges in the small regions are as rectilinear as possible. Note, however, that when the small regions are too small such that the number of small regions increases, a processing time also increases, and therefore the small regions are preferably made as small as possible while taking into consideration a balance between the continuity evaluation and the processing time. The shape of the small regions is not limited to a lattice shape, and any desired shape, such as a circular shape or a hexagonal shape, may be used. Further, overlap and gaps may exist between the small regions, but to facilitate the continuity evaluation between adjacent small regions, to be described below, the overlap and gaps are preferably small.

The frequency analysis unit 32 performs a frequency analysis on each small region. Any type of transform that can handle periodicity, such as a two-dimensional Fourier transform, a two-dimensional Walsh Hadamard transform, or a discrete cosine transform, for example, may be used as the frequency analysis. In this embodiment, a case in which a two-dimensional Fourier transform is used as the frequency analysis will be described. Note that when a type of frequency analysis other than a two-dimensional Fourier transform is used, processing can be performed in accordance with a case in which a two-dimensional Fourier transform is used.

The frequency analysis unit 32 converts a luminance value of each small region into a frequency component, such as an amplitude component or a phase component, in a frequency space by performing a two-dimensional Fourier transform on the luminance value.

Figure 3:
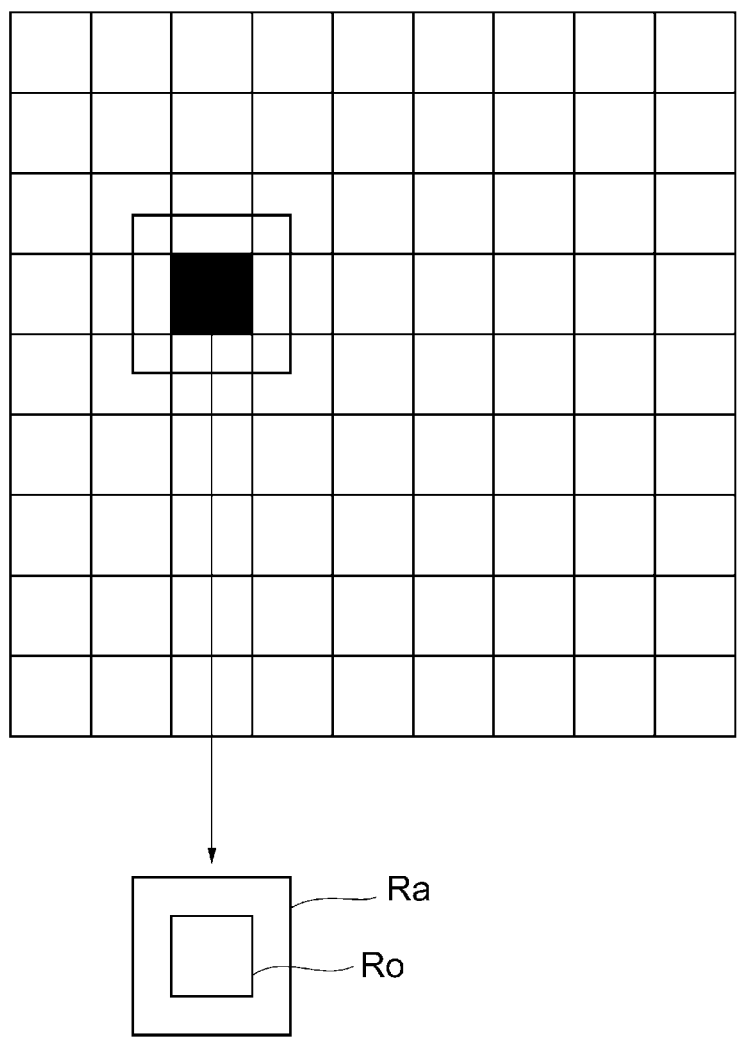
FIG. 3 is a view showing a range of a frequency analysis subject.

Note that while the small region itself may be the subject of the frequency analysis, a region Ra also including a periphery of a subject small region Ro, as shown in FIG. 3, may also be used as the frequency analysis subject. When the frequency analysis subject region is too small, the number of fingerprint ridges in the region decreases, making it difficult to identify periodicity. On the other hand, the fingerprint ridges are curved, and therefore, when the frequency analysis subject region is too large, a curvature of the fingerprint ridges in the region increases, making it difficult to grasp the periodicity. Hence, the size of the frequency analysis subject region is preferably set such that three to five fingerprint ridges are included therein. Further, by including the periphery of the small region in the frequency analysis subject region, the small region can be reduced in size while maintaining stability in the frequency analysis.

The ridge candidate extraction unit 33 extracts frequency components corresponding to ridge candidates in each small region from the frequency components determined by the frequency analysis performed on each small region. More specifically, the ridge candidate extraction unit 33 extracts the ridge candidates included in each small region by extracting a group of local maximum points from the frequency components expressed on the frequency space by the two-dimensional Fourier transform. When a plurality of groups of local maximum points exist in a single small region, ridge candidates corresponding to the respective groups are extracted.

Figure 5A:
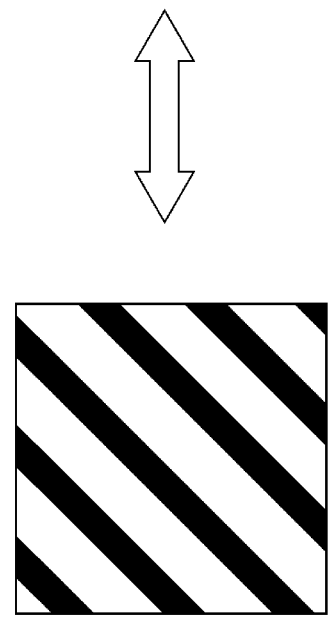
FIG. 5 is a view showing a relationship between the two-dimensional sine wave and a frequency space.
Figure 5B:
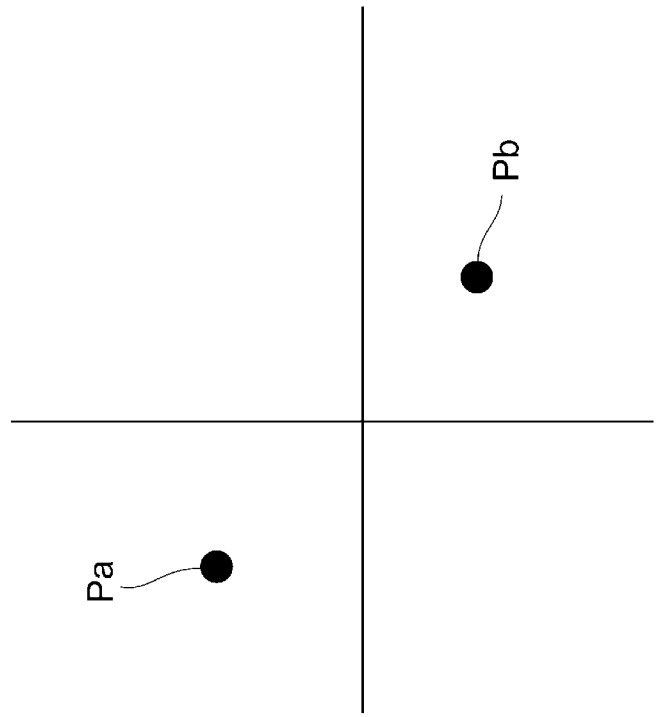

As shown in FIG. 4A, when a frequency analysis subject region R is sufficiently small, a ridge pattern of a fingerprint can be approximated by a two-dimensional sine wave shown in FIG. 4B. When a two-dimensional sine wave shown in FIG. 5A is represented in a frequency space, a group of origin symmetrical points (a group including a point Pa and a point Pb) shown in FIG. 5B is obtained. In other words, in a frequency space obtained by performing a two-dimensional Fourier transform on a fingerprint ridge, the fingerprint ridge is expressed as a group of points corresponding to a direction and a width of the fingerprint ridge. Hence, a single group of local maximum points in a frequency space serves as a frequency component representing a fingerprint ridge.

As shown in FIG. 16, in a region where a transparent thin film F is adhered to a finger surface T, a false ridge pattern on the thin film is superimposed on a true ridge pattern on the skin, and therefore a pattern in which two two-dimensional sine waves overlap is observed. When a region R shown in FIG. 6A is represented in a frequency space, two groups of points (a group including the point Pa and the point Pb and a group including a point Pc and a point Pd) shown in FIG. 6B are obtained. On an image in which a plurality of two-dimensional sine waves overlap in this manner, by determining the groups of points corresponding to the respective two-dimensional sine waves as groups of local maximum points representing amplitudes in the frequency space, two-dimensional sine waves corresponding to the respective groups of local maximum points, such as those shown in FIGS. 6C and 6D, can be determined.

A ridge candidate search range may be set as the entire range of the frequency space, or limited to a range including only wavelengths within a specific range such that selections are not made outside this range. It is known that intervals between ridges on a human fingerprint are limited to a specific range (between approximately 0.2 mm and 1.4 mm, for example). Therefore, by limiting the search range to this specific range, candidates not derived from fingerprint ridges, for example candidates having a short wavelength such as noise and candidates having a long wavelength due to overall luminance variation and the like, can be excluded, enabling an improvement in the precision with which the ridge candidates are selected.

Further, candidates that correspond to local maximum points but whose amplitude is smaller than a predetermined amplitude may be excluded from the ridge candidates. The reason for this is that a fingerprint ridge is not a perfect two-dimensional sine wave, and therefore local maximum points may be calculated in a location of the frequency space other than the location of a group of local maximum points corresponding to a two-dimensional sine wave, in accordance with a difference from the two-dimensional sine wave. Further, noise such as thinning is also included in the captured image, and therefore local maximum points may also be calculated in locations corresponding to this noise. These surplus local maximum points normally have a considerably smaller amplitude than local maximum points corresponding to ridges, and therefore, by excluding local maximum points having an amplitude that is smaller than a predetermined value from the ridges candidates, the effect of surplus ridge candidates generated by noise and the like can be removed. As a result, the precision of the false finger determination can be improved. A minimum value of an amplitude at which a local maximum point corresponding to a ridge can be extracted, for example, may be used as the aforesaid predetermined value.

The continuous ridge candidate group generation unit 34 compares ridge candidates between adjacent small regions to evaluate the continuity thereof, and generates a continuous ridge candidate group by gathering together ridge candidates considered to be derived from an identical ridge.

Although a fingerprint ridge is not a perfect straight line, a ridge direction does not vary dramatically except in a part known as a core in the center of the fingerprint and a part known as a delta on a side of the fingerprint. Therefore, a pattern of a ridge spanning adjacent small regions can be approximated easily. When ridge candidates in the frequency space are derived from an identical ridge, the directions, widths, and amplitudes of the ridge candidates are close in value. Therefore, as shown in FIG. 7, the continuous ridge candidate group generation unit 34 generates continuous ridge candidate groups G1, G2 by comparing the directions, widths, amplitudes, and so on of ridge candidates between adjacent small regions R1, R2 and gathering together ridge candidates having directions, widths, amplitudes, and so on that differ from each other by less than a predetermined value. A maximum value of a value that can be obtained between ridge candidates derived from an identical ridge, for example, may be used as the aforesaid predetermined value.

When a plurality of continuous ridge candidate groups exist, the continuous ridge candidate group generation unit 34 integrates continuous ridge candidate groups including shared ridge candidates into a single continuous ridge candidate group.

Figure 8:
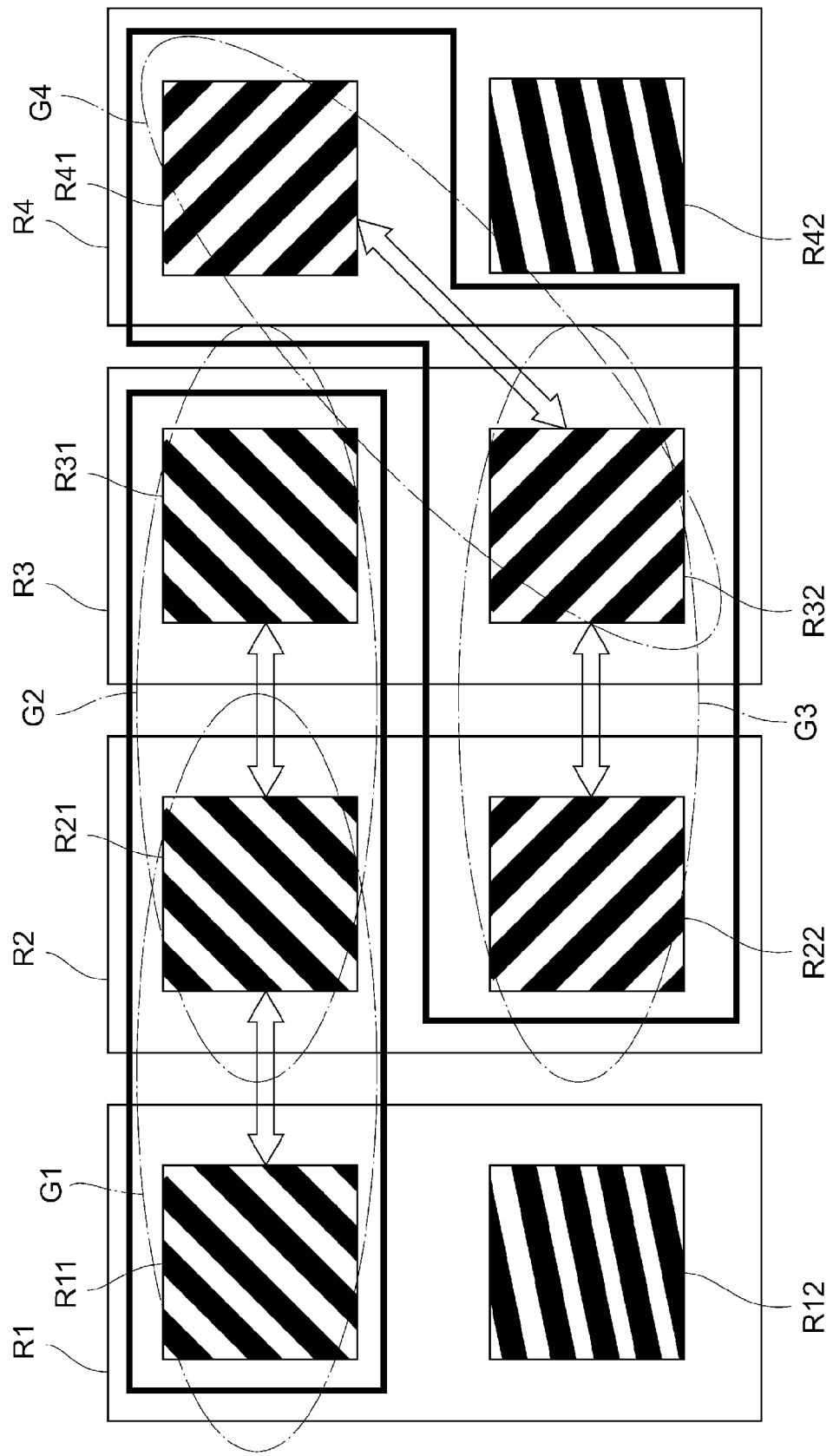
FIG. 8 is a view illustrating an example of integration of the continuous ridge candidate group.

As shown in FIG. 8, for example, when a ridge candidate R11 in a small region R1 forms a continuous ridge candidate group G1 with a ridge candidate R21 in a small region R2 adjacent to the small region R1 and the ridge candidate R21 in the small region R2 forms a continuous ridge candidate group G2 with a ridge candidate R31 in a small region R3 adjacent to the small region R2, the ridge candidate R21 is shared by the two groups, and therefore the ridge candidate R11, the ridge candidate R21, and the ridge candidate R31 are integrated into the single continuous ridge candidate group G1.

Similarly, when a ridge candidate R22 in the small region R2 forms a continuous ridge candidate group G3 with a ridge candidate R32 in the small region R3 adjacent to the small region R2 and the ridge candidate R32 in the small region R3 forms a continuous ridge candidate group G4 with a ridge candidate R41 in a small region R4 adjacent to the small region R3, the ridge candidate R32 is shared by the two groups, and therefore the ridge candidate R22, the ridge candidate R32, and the ridge candidate R41 are integrated into the single continuous ridge candidate group G3.

By successively integrating the continuous ridge candidate groups including shared ridge candidates, the ridge candidates can be combined into several continuous ridge candidate groups.

Note that in FIG. 8, a case in which laterally arranged small regions are compared is illustrated, but a comparison range is not limited to laterally adjacent regions, and may include four laterally and longitudinally proximal regions or eight proximal regions including diagonal directions. In such cases, processing can be performed similarly.

Figure 9:
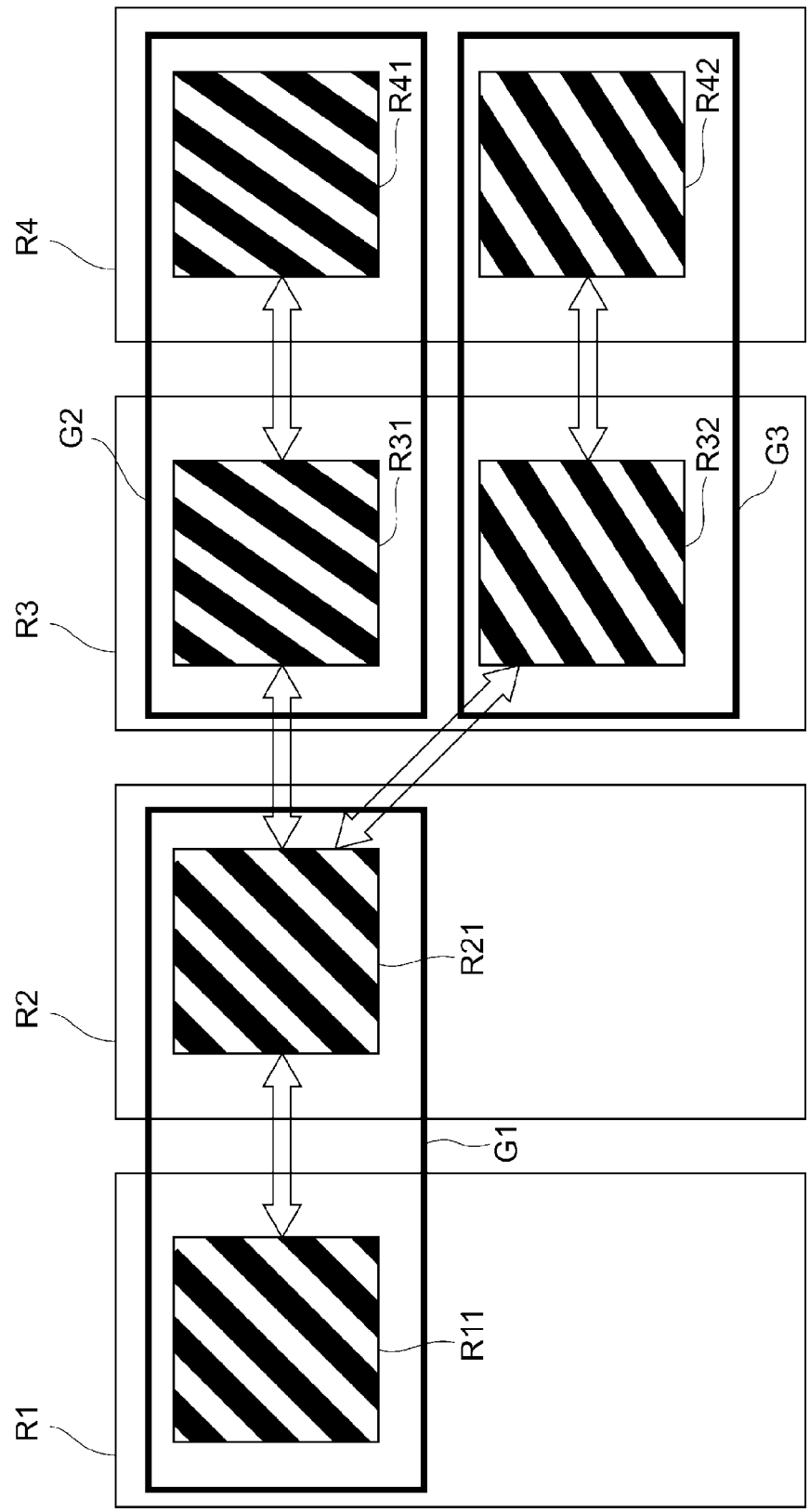
FIG. 9 is a view showing a case in which a single ridge candidate is included in a plurality of continuous ridge candidate groups.

The continuous ridge candidate group generation unit 34 ensures that a single ridge candidate is not included in a plurality of continuous ridge candidate groups. When a continuous ridge candidate group is created, a single ridge candidate may be evaluated as possessing a continuity with a plurality of ridge candidates in an adjacent small region. For example, a ridge candidate R21 in a small region R2 shown in FIG. 9 may be evaluated as possessing continuity with both a ridge candidate R31 and a ridge candidate R32 in a small region R3 adjacent to the small region R2. In this case, the continuous ridge candidate group generation unit 34 eliminates a continuity relationship between the small region R2 and the small region R3, and generates three continuous ridge candidate groups, namely a continuous ridge candidate group G1 including a ridge candidate R11 and the ridge candidate R21, a continuous ridge candidate group G2 including the ridge candidate R31 and a ridge candidate R41, and a continuous ridge candidate group G3 including the ridge candidate R32 and a ridge candidate R42.

Figure 10:
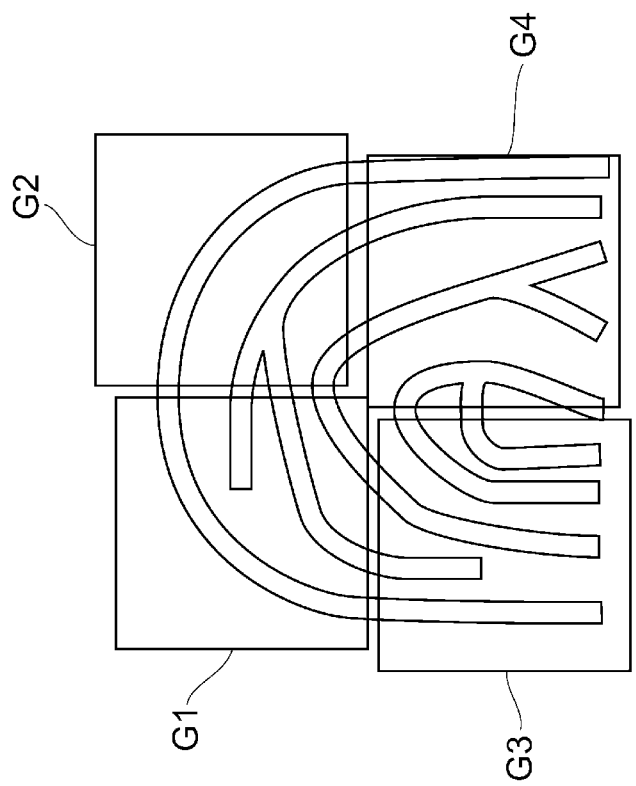
FIG. 10 is a view showing a case in which a correct ridge is divided between a plurality of continuous ridge candidate groups.

Fingerprint ridges are normally continuous, and therefore a single continuous ridge candidate group is ideally generated from an entire correct ridge. However, in addition to the continuity relationship between the plurality of ridge candidates described above, parts having a comparatively large curvature and divisions caused by wrinkles, noise, and so on also exist. In this case, as shown in FIG. 10, for example, a continuous ridge candidate group corresponding to a correct ridge is divided into a plurality of continuous ridge candidate groups G1, G2, G3, G4.

Ridge candidates generated by noise such as image thinning are unlikely to appear continuously in adjacent small regions, and therefore a continuous ridge candidate group constituted by such ridge candidates tends to be small in size. Hence, the continuous ridge candidate group generation unit 34 determines that a continuous ridge candidate group in which the number of ridge candidates included in the continuous ridge candidate group (the size of the continuous ridge candidate group) is smaller than a predetermined number is a continuous ridge candidate group generated by noise, and removes this continuous ridge candidate group from the continuous ridge candidate groups.

Figure 11:
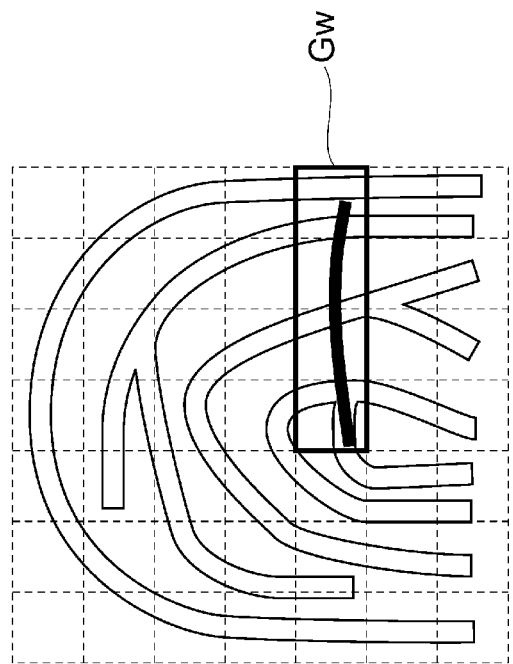
FIG. 11 is a view showing a continuous ridge candidate group constituted by ridge candidates of a wrinkle.

As shown in FIG. 11, a continuous ridge candidate group Gw constituted by ridge candidates derived from a wrinkle is long in an extension direction of the wrinkle but short in a perpendicular direction to the extension direction of the wrinkle. Hence, the continuous ridge candidate group generation unit 34 determines that a continuous ridge candidate group having a width in a perpendicular direction to a direction of the ridge candidates included in the continuous ridge candidate group that is smaller than a predetermined value is a continuous ridge candidate group generated by a wrinkle, and removes this continuous ridge candidate group from the continuous ridge candidate groups.

When overlap of at least a predetermined size (image area) exists between the image regions corresponding to the continuous ridge candidate group, the determination unit 35 determines that an image of a false finger formed by attaching a transparent thin film to a surface of a finger has been captured. When overlap of at least the predetermined size does not exist between the image regions corresponding to the continuous ridge candidate group, on the other hand, the determination unit 35 determines that an image of a finger of an individual has been captured. A minimum value of a size that can be considered indicative of a case in which a transparent thin film has been adhered to the surface of a finger, for example, may be used as the predetermined size.

Figure 12:
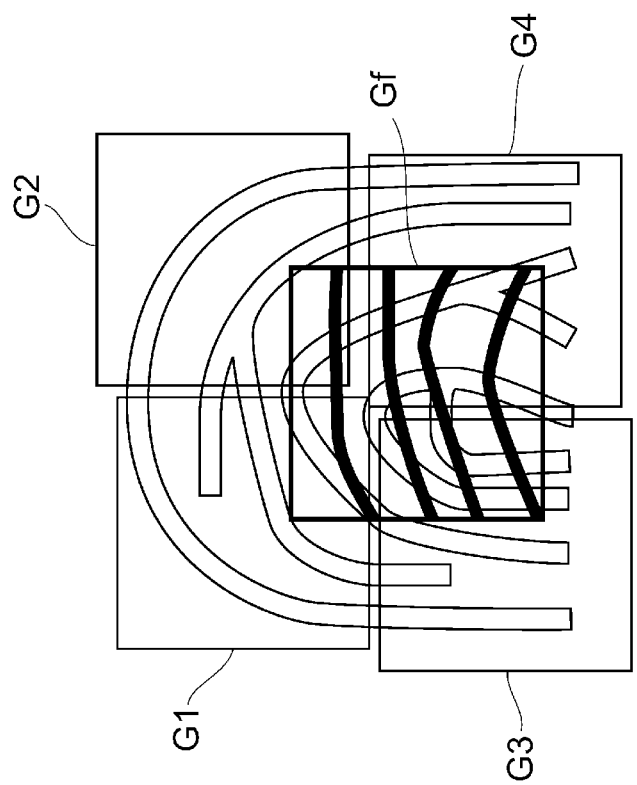
FIG. 12 is a view showing a condition in which a continuous ridge candidate group of a fingerprint ridge and a continuous ridge candidate group of a false ridge overlap in a thin film part.

In the case of a normal fingerprint, as shown in FIG. 10, no overlap occurs between the continuous ridge candidate groups G1, G2, G3, G4 even when a continuous ridge candidate group derived from a correct ridge is divided into a plurality. In a case where a transparent thin film is adhered to the surface of a finger, as shown in FIG. 16, on the other hand, the ridge pattern generated by the true fingerprint and the false ridge pattern generated by the thin film are superimposed in the thin film F part. In this case, as shown in FIG. 12, overlap occurs in the thin film part between the continuous ridge candidate groups G1, G2, G3, G4 derived from the true fingerprint ridges and a continuous ridge candidate group Gf derived from the false ridges on the thin film. Hence, by checking for overlap between continuous ridge candidate groups, it is possible to determine whether or not a transparent thin film has been adhered to the surface of a finger.

Note that a predetermined function may be used as a reference for determining a degree of overlap between image regions. A function that returns a larger value (an increasing likelihood of a false finger) as an overlap size applied as an argument increases or a function that returns a larger value (an increasing likelihood of a normal finger) as an overlap size applied as an argument decreases, for example, may be used as the predetermined function.

Figure 13:
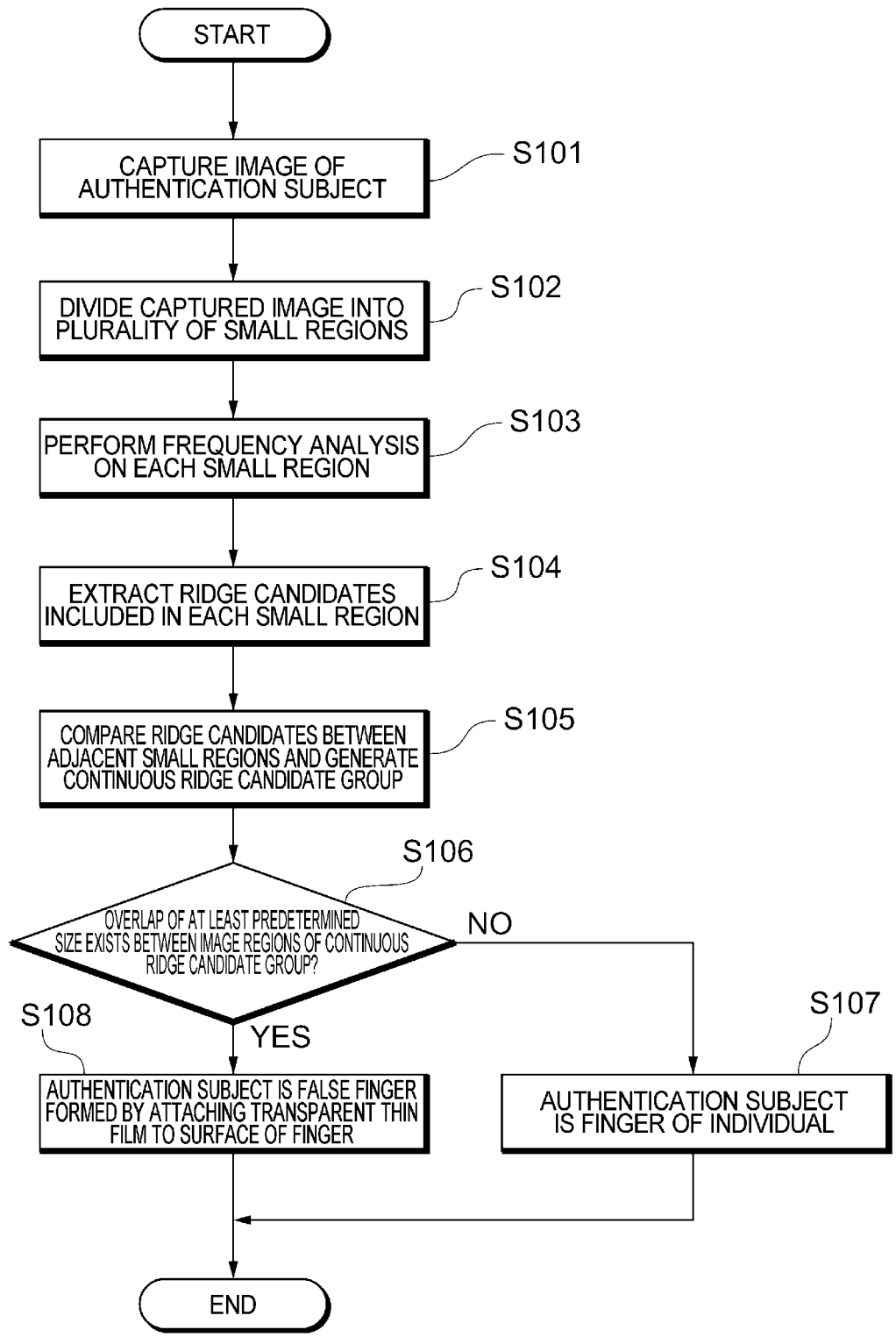
FIG. 13 is a flowchart showing processing procedures of false finger determination processing executed by the fingerprint authentication system according to the first embodiment.

Next, referring to FIG. 13, false finger determination processing executed by the fingerprint authentication system according to the first embodiment will be described. FIG. 13 is a flowchart showing processing procedures executed to determine a false finger formed by attaching a transparent thin film to a surface of a finger.

First, when an authentication subject is placed in the placement region of the fingerprint authentication system 1, the light source unit 20 irradiates the authentication subject with light, whereupon the imaging unit 10 captures an image of the authentication subject (Step S101).

Next, the image division unit 31 divides the image captured by the imaging unit 10 into a plurality of small regions (Step S102).

Next, the frequency analysis unit 32 executes frequency analysis by performing a two-dimensional Fourier transform on the luminance values of the image for each small region (Step S103).

Next, the ridge candidate extraction unit 33 extracts ridge candidates included in each small region by extracting groups of local maximum points from the frequency components expressed on the frequency space by the two-dimensional Fourier transform (Step S104).

Next, the continuous ridge candidate group generation unit 34 evaluates continuity by comparing the ridge candidates between adjacent small regions, and generates a continuous ridge candidate group by gathering together ridge candidates considered to be derived from an identical ridge (Step S105).

Next, the determination unit 35 determines whether or not overlap of at least the predetermined size exists between the image regions corresponding to the continuous ridge candidate group (Step S106). When the determination is negative (Step S106: NO), the determination unit 35 determines that the authentication subject is a finger of an individual (Step S107). In this case, the false finger determination processing is terminated. Thereafter, the fingerprint authentication system 1 executes fingerprint authentication processing.

When, on the other hand, overlap of at least the predetermined size is determined to exist between the image regions corresponding to the continuous ridge candidate group in the determination of Step S106 (Step S106: YES), the determination unit 35 determines that the authentication subject is a false finger formed by attaching a transparent thin film to a surface of a finger (Step S108). The false finger determination processing is then terminated.

With the fingerprint authentication system 1 according to the first embodiment, described above, local maximum points on a frequency space are determined by performing a two-dimensional Fourier transform in each of a plurality of small regions obtained by dividing a captured image of an authentication subject, a continuous ridge candidate group constituted by ridge candidates considered to be derived from an identical ridge is generated using the local maximum points, and when overlap exists between the image regions corresponding to the continuous ridge candidate group, it can be determined that the authentication subject is a false finger formed by attaching a transparent thin film to a surface of a finger. Therefore, in a case where a false finger formed by attaching a transparent thin film to a surface of a finger is used as the authentication subject, the false finger can be detected when a thin film having a different pattern to a true ridge pattern is attached to the surface of the finger. As a result, the precision with which a false finger formed by attaching a transparent thin film to a surface of a finger is determined can be improved.

Second Embodiment

Figure 14:
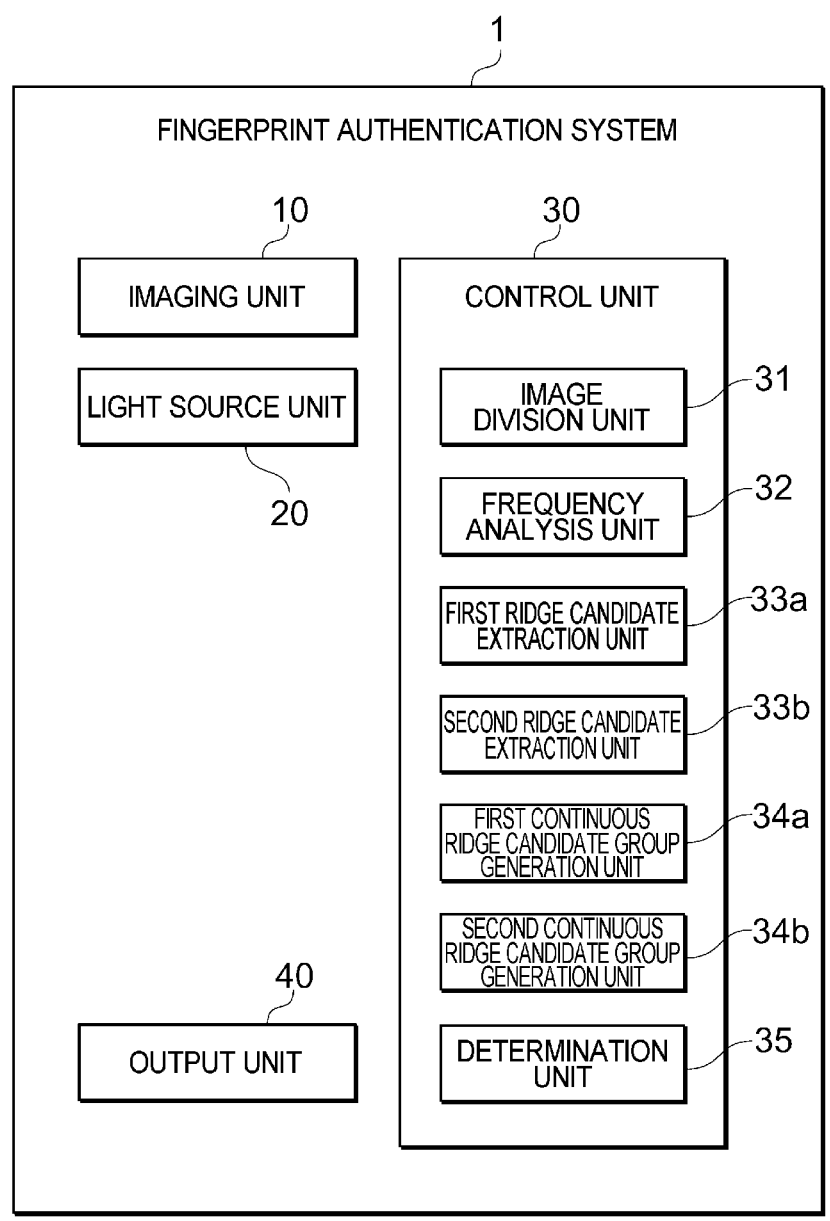
FIG. 14 is a block diagram showing a schematic configuration of a fingerprint authentication system according to a second embodiment.

A second embodiment of the present invention will now be described. FIG. 14 is a block diagram showing a configuration of a fingerprint authentication system according to the second embodiment. The fingerprint authentication system 1 according to the second embodiment differs from the fingerprint authentication system 1 according to the first embodiment in a part of the functions of the control unit 30. More specifically, the fingerprint authentication system 1 according to the second embodiment differs from the fingerprint authentication system 1 according to the first embodiment in that the ridge candidate extraction unit 33 is replaced by a first ridge candidate extraction unit 33a and a second ridge candidate extraction unit 33b, the continuous ridge candidate group generation unit 34 is replaced by a first continuous ridge candidate group generation unit 34a and a second continuous ridge candidate group generation unit 34b, and the functions of the determination unit 35 are different. All other configurations are similar to the configurations of the fingerprint authentication system according to the first embodiment, and therefore identical reference symbols have been allocated to identical constituent elements and description thereof has been omitted. The following description focuses mainly on differences with the first embodiment.

The first ridge candidate extraction unit 33a and the second ridge candidate extraction unit 33b are similar to the ridge candidate extraction unit 33 of the first embodiment in that they extract ridge candidates included in each small region by performing a two-dimensional Fourier transform to extract groups of local maximum points from the frequency components expressed on the frequency space, but differ therefrom as follows.

The first ridge candidate extraction unit 33a extracts ridge candidates having a large amplitude from among the ridge candidates included in the respective small regions. The second ridge candidate extraction unit 33b extracts ridge candidates having a small amplitude from among the ridge candidates included in the respective small regions. The size of the amplitude can be determined from the size of the local maximum points on the frequency space. Hence, for example, when the size of the local maximum points equals or exceeds a predetermined value, the amplitude can be determined to be large, and when the size of the local maximum points is smaller than the predetermined value, the amplitude can be determined to be small. For example, maximum values of the local maximum points within a range of wavelengths corresponding to a ridge in the frequency space may be determined for each of the respective small regions, and an average value thereof or a value obtained by multiplying the average value by a predetermined coefficient may be used as the predetermined value.

Here, in a small region including only ridges of a correct fingerprint, the ridges are clear, and therefore the amplitude in the frequency space is large. In a small region where ridges of a correct fingerprint intermix with false ridges on a transparent thin film, on the other hand, the respective ridges are unclear, and therefore the amplitude in the frequency space is smaller than that of a case in which only ridges of a correct fingerprint exist. More specifically, the fingerprint pattern on the finger surface is photographed through the transparent thin film, and therefore the light attenuates in the thin film such that the amplitude in the frequency space of the fingerprint pattern on the finger surface becomes smaller than that of the false fingerprint pattern.

By providing the first ridge candidate extraction unit 33a and the second ridge candidate extraction unit 33b, ridge candidates can be extracted separately in accordance with the size of the amplitude as follows. In a region where only ridges of a correct fingerprint exist, the local maximum points corresponding to the ridges of the correct fingerprint can be extracted as ridge candidates by the first ridge candidate extraction unit 33a. In a small region where ridges of a correct fingerprint intermix with false ridges on a transparent thin film, the local maximum points corresponding to the ridges of the correct fingerprint can be extracted as ridge candidates by the second ridge candidate extraction unit 33b. The local maximum points corresponding to the false ridges on the transparent thin film, meanwhile, are extracted as ridge candidates by either the first ridge candidate extraction unit 33a or the second ridge candidate extraction unit 33b, depending on the condition of the false finger and so on.

The first continuous ridge candidate group generation unit 34a and the second continuous ridge candidate group generation unit 34b are similar to the continuous ridge candidate group generation unit 34 of the first embodiment in that they evaluate continuity by comparing ridge candidates between adjacent small regions and generate a continuous ridge candidate group by gathering together ridge candidates considered to be derived from an identical ridge, they integrate continuous ridge candidate groups including shared ridge candidates into a single continuous ridge candidate group when a plurality of continuous ridge candidate groups exist, and they ensure that a single ridge candidate is not included in a plurality of continuous ridge candidate groups, but differ therefrom as follows.

The first continuous ridge candidate group generation unit 34a generates a first continuous ridge candidate group by comparing the ridge candidates extracted by the first ridge candidate extraction unit 33a. The second continuous ridge candidate group generation unit 34a generates a second continuous ridge candidate group by comparing the ridge candidates extracted by the second ridge candidate extraction unit 33b.

The determination unit 35 is similar to the determination unit 35 of the first embodiment in that it determines whether or not an image of a false finger formed by attaching a transparent thin film to a surface of a finger has been captured on the basis of whether or not overlap of at least the predetermined size exists between the image regions corresponding to the continuous ridge candidate group, but differs therefrom as follows.

When overlap of at least the predetermined size exists between an image region corresponding to the first continuous ridge candidate group and an image region corresponding to the second continuous ridge candidate group, or when overlap of at least the predetermined size exists between the image regions corresponding to the second continuous ridge candidate group, the determination unit 35 determines that an image of a false finger formed by attaching a transparent thin film to a surface of a finger has been captured. When, on the other hand, overlap of at least the predetermined size does not exist under both of the above conditions, the determination unit 35 determines that an image of a finger of an individual has been captured.

The reason why the determination can be made in this manner is as follows. The ridge candidates extracted by the first ridge candidate extraction unit 33a may include local maximum points corresponding to a ridge of a correct fingerprint in a small region including only ridges of a correct fingerprint and local maximum points corresponding to a false ridge on a transparent thin film in a small region where ridges of a correct fingerprint intermix with false ridges on a transparent thin film. On the other hand, the ridge candidates extracted by the second ridge candidate extraction unit 33b may include local maximum points corresponding to a ridge of a correct fingerprint in a small region where ridges of a correct fingerprint intermix with false ridges on a transparent thin film and local maximum points corresponding to a false ridge on a transparent thin film in a small region where ridges of a correct fingerprint intermix with false ridges on a transparent thin film.

In other words, overlap between a ridge of a correct fingerprint and a false ridge in a small region where ridges of a correct fingerprint intermix with false ridges on a transparent thin film can appear between an image region corresponding to the first continuous ridge candidate group and an image region corresponding to the second continuous ridge candidate group or between image regions corresponding to the second continuous ridge candidate group. Hence, by performing the determination in this manner, an overlap determination between the image regions corresponding to the first continuous ridge candidate group can be omitted.

Figure 15:
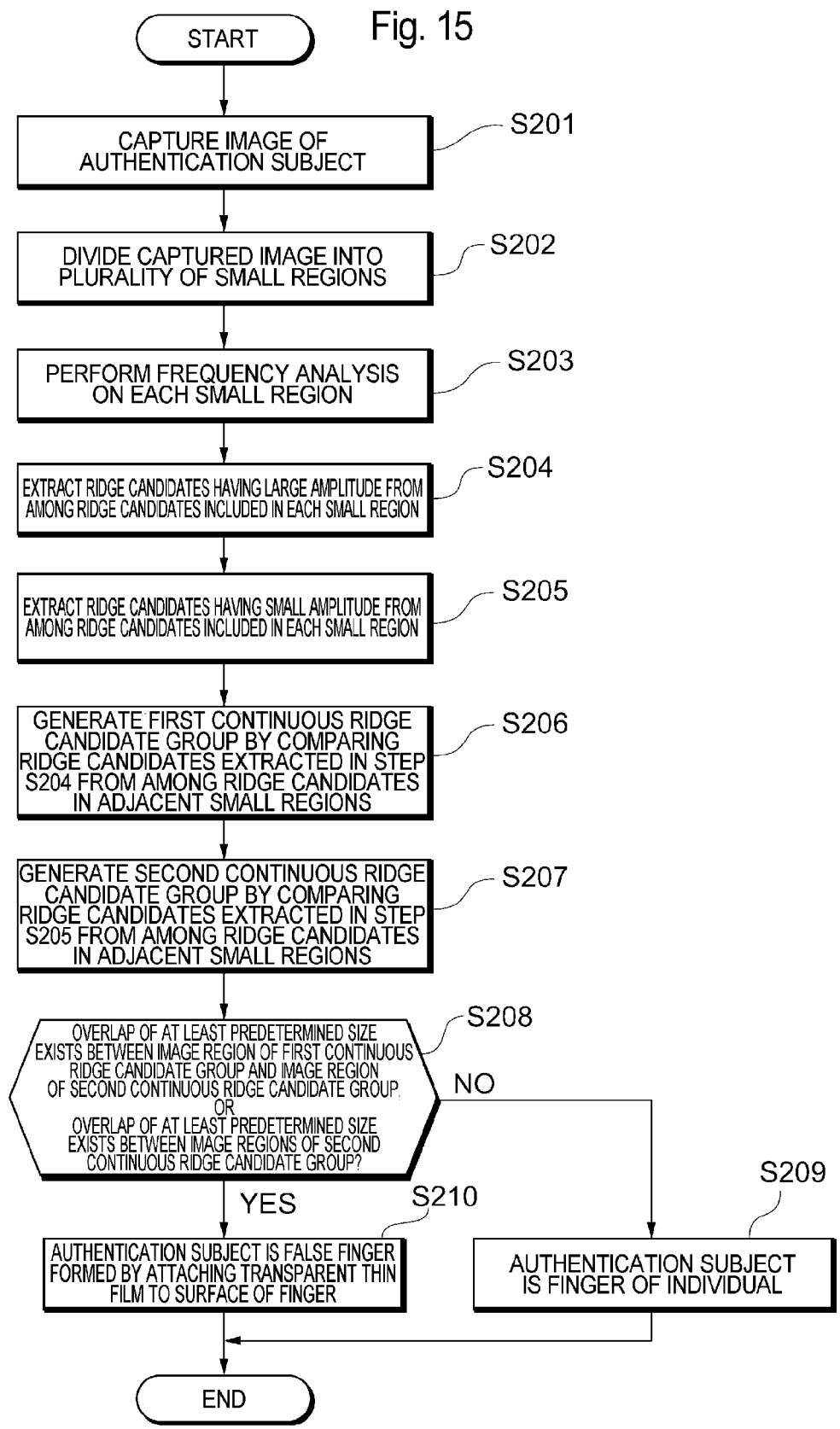
FIG. 15 is a flowchart showing processing procedures of false finger determination processing executed by the fingerprint authentication system according to the second embodiment.

Next, referring to FIG. 15, false finger determination processing executed by the fingerprint authentication system according to the second embodiment will be described. FIG. 15 is a flowchart showing processing procedures executed to determine a false finger formed by attaching a transparent thin film to a surface of a finger. Note that Steps S201 to S203 in FIG. 15 are similar in processing content to Steps S101 to S103 in FIG. 13, and therefore description thereof has been omitted. The following description focuses mainly on processing content of Step S204 onward, which differs from FIG. 13.

When the frequency analysis is performed on each small region in Step S203 of FIG. 15, the first ridge candidate extraction unit 33a extracts ridge candidates having a large amplitude from among the ridge candidates included in the respective small regions by extracting groups of local maximum points having a local maximum point size of at least the predetermined value from the frequency components expressed on the frequency space by the two-dimensional Fourier transform (Step S204).

Next, the second ridge candidate extraction unit 33b extracts ridge candidates having a small amplitude from among the ridge candidates included in the respective small regions by extracting groups of local maximum points having a local maximum point size of less than the predetermined value from the frequency components expressed on the frequency space by the two-dimensional Fourier transform (Step S205).

Next, the first continuous ridge candidate group generation unit 34a evaluates continuity by comparing the ridge candidates between adjacent small regions, from among the ridge candidates having a large amplitude extracted in Step S204, and generates the first continuous ridge candidate group by gathering together the ridge candidates considered to be derived from an identical ridge (Step S206).

Next, the second continuous ridge candidate group generation unit 34b evaluates continuity by comparing the ridge candidates between adjacent small regions, from among the ridge candidates having a small amplitude extracted in Step S205, and generates the second continuous ridge candidate group by gathering together the ridge candidates considered to be derived from an identical ridge (Step S207).

Next, the determination unit 35 determines whether or not overlap of at least the predetermined size exists between an image region corresponding to the first continuous ridge candidate group and an image region corresponding to the second continuous ridge candidate group or whether or not overlap of at least the predetermined size exists between the image regions corresponding to the second continuous ridge candidate group (Step S208). When the determination is negative (Step S208: NO), the determination unit 35 determines that the authentication subject is a finger of an individual (Step S209). In this case, the false finger determination processing is terminated. Thereafter, the fingerprint authentication system 1 executes fingerprint authentication processing.

When, on the other hand, at least one of the conditions is satisfied in the determination of Step S208 (Step S208: YES), the determination unit 35 determines that the authentication subject is a false finger formed by attaching a transparent thin film to a surface of a finger (Step S210). The false finger determination processing is then terminated.

With the fingerprint authentication system 1 according to the second embodiment, described above, the following effects can be obtained in addition to the effects obtained with the fingerprint authentication system 1 according to the first embodiment. When determining the degree of overlap between the continuous ridge candidate groups, the overlap determination between the image regions corresponding to the first continuous ridge candidate group can be omitted, and therefore a processing time of the false finger determination processing can be shortened. Further, when evaluating the continuity of the ridge candidates, an evaluation is not performed between a ridge candidate having a large amplitude and a ridge candidate having a small amplitude, and therefore a situation in which a candidate corresponding to a true fingerprint and a candidate corresponding to a false fingerprint happen to have a similar direction and so on and are therefore included in the same continuous ridge candidate group can be avoided.

Modified Examples

Note that the embodiments described above are merely examples and do not exclude various amendments and technical applications not described explicitly in the embodiments. In other words, the present invention may be implemented after undergoing various amendments within a scope that does not depart from the spirit thereof.

For example, in the above embodiments, a case in which the present invention is applied to a biometric authentication system for authenticating a registrant using a fingerprint was described, but the present invention is not limited thereto, and may be applied to any system that uses fingerprint authentication, for example a system for checking fingerprints in a criminal database or the like.

Further, in the above embodiments, the continuous ridge candidate group generation unit 34 (including the first continuous ridge candidate group generation unit 34a and the second continuous ridge candidate group generation unit 34b) generates a continuous ridge candidate group by gathering together ridge candidates that differ from each other in direction, width, amplitude, and so on by less than a predetermined value, but the continuous ridge candidate group generation unit 34 is not limited thereto and may generate a continuous ridge candidate group by gathering together ridge candidates in which a ratio between the directions, widths, amplitudes, and so on thereof is smaller than a predetermined value, for example. When a difference is used, the difference tends to increase as an absolute value increases, and therefore, if a determination is made using an identical threshold (predetermined value) the precision of the determination deteriorates. For example, at a constant difference of 0.1 mm, the effect of the difference is greater in a case where the width of the ridge is 0.2 mm than in a case where the width of the ridge is 1.4 mm. Using a ratio, therefore, the precision of the determination can be improved. Alternatively, the threshold may be varied in accordance with the values of the directions, widths, amplitudes, and so on of the ridge candidates.

Further, when generating the continuous ridge candidate group, the continuity may be evaluated by comparing a part of the directions, widths, and amplitudes of the ridge candidates. For example, the amplitude of the ridge may vary due to noise or pressing pressure depending on the arrangement of the fingerprint sensor or the like. Therefore, by using only the direction and the width and omitting the amplitude when the amplitude is unstable, an improvement can be achieved in the precision of the continuity evaluation. Further, a phase of the ridge candidates in the frequency space may be used in addition to the direction, width, and amplitude of the ridge candidates. For example, when ridge candidates deviate from each other by half the ridge width in a perpendicular direction to the ridge direction, the ridge candidates are highly unlikely to correspond to continuous ridges, even if the directions, widths, and amplitudes thereof are identical. By using the phase in this case, it can be determined that the phase deviates by $\pi/2$, and therefore the continuity of the ridge candidates can be denied.

Furthermore, in the above embodiments, an image obtained when the light from the light source unit 20 is reflected by the finger surface is captured by the imaging unit 10, and this reflected light image is used as the input image. However, the present invention is not limited thereto, and an image obtained when the light from the light source unit 20 passes through the interior of the finger may be captured by the imaging unit 10, and this transmitted light image may be used as the input image. In this case, the arrangement of the light source unit 20, the imaging unit 10, and the placement region is designed such that an image obtained when the light from the light source unit 20 passes through the interior of the finger can be captured by the imaging unit 10.

Further, the imaging unit 10 is not limited to a CCD camera, and any imaging device that can capture an image of a wavelength region of a light source may be used. The imaging unit 10 may be integrated with an imaging device for capturing a fingerprint image used for fingerprint authentication, or separate imaging devices may be used. Moreover, the light source unit 20 is not limited to an LED, and any light source that emits light having a wavelength that is reflected by a finger (in a case where a reflected light image is captured) or transmitted through a finger (in a case where a transmitted light image is captured), such as white light or infrared light, may be employed.

Furthermore, the output unit 40 is not limited to a warning lamp, and a display device such as a display, for example, may be used such that when the authentication subject is determined to be a false finger, a message, a color, a brightness change, or the like indicating this is displayed on the display device. Further, the present invention is not limited to a configuration in which detection of a false finger is output to a warning lamp or a display device, and instead, a signal including a determination result may be output to another authentication system connected via a network, for example. In this case, when the authentication subject is determined to be a false finger, authentication is not performed by the other authentication system. Moreover, the present invention is not limited to a configuration in which detection of a false finger is output, and instead, for example, the determination unit may determine a likelihood indicating the likelihood of the presence of a false finger and vary the length of a warning sound, the color, the brightness, and so on in accordance with the likelihood.

Furthermore, in the above embodiments, the present invention is applied to a case in which a false finger formed by adhering a transparent thin film to a surface of a finger is detected, but the present invention is not limited thereto and may also be applied to a case in which, when the fingerprint of a user subjected to fingerprint authentication previously remains on a surface of the fingerprint sensor, the existence of the remaining fingerprint is detected, for example. When the remaining fingerprint exists, the ridge pattern of the true fingerprint and a ridge pattern of the remaining fingerprint are measured while superimposed, and therefore a similar image to that of the above embodiments, in which a transparent thin film exists, is input. Hence, by executing similar processing to the false finger determination processing of the above embodiments, the presence of a remaining fingerprint can be determined. Accordingly, the present invention may be applied to a fingerprint authentication system that detects the presence of a different pattern to the ridge pattern of a registrant as an abnormality.

Moreover, the fingerprint authentication system according to the above embodiments includes the respective constituent elements shown in FIG. 1 or FIG. 14, but the fingerprint authentication system does not necessarily have to include all of these elements. For example, the fingerprint authentication system may include at least the control unit 30. In this case, the imaging unit 10, the light source unit 20, and the output unit 40 may be provided separately on the exterior of the fingerprint authentication system.

Finally, a part or all of the embodiments described above may be described as follows. However, the present invention is not limited to the following description.

(Note 1) A fingerprint authentication system including: an image division unit that divides a captured image of an authentication subject to be subjected to fingerprint authentication into a plurality of small regions; a frequency analysis unit that performs a frequency analysis on each of the small regions; a ridge candidate extraction unit that extracts frequency components corresponding to ridge candidates in the small regions from frequency components obtained in the frequency analysis; a continuous ridge candidate group generation unit that compares the ridge candidates between adjacent small regions, and when the ridge candidates satisfy a condition enabling the ridge candidates to be determined continuous, generates a continuous ridge candidate group including the ridge candidates; and a determination unit that determines that an abnormality exists in the image when overlap exists between the image regions corresponding to the continuous ridge candidate group.

(Note 2) The fingerprint authentication system according to Note 1, wherein the frequency analysis unit performs a two-dimensional Fourier transform as the frequency analysis, and the ridge candidate extraction unit extracts a group of local maximum points having origin symmetry when expressed on a frequency space by the two-dimensional Fourier transform as the frequency components corresponding to the ridge candidates.

(Note 3) The fingerprint authentication system according to Note 1 or 2, wherein the condition enabling the ridge candidates to be determined continuous is satisfied when a difference or a ratio between values of at least a part of a direction, a width, an amplitude, and a phase of the ridge candidates is smaller than a predetermined value.

(Note 4) The fingerprint authentication system according to any one of Notes 1 to 3, wherein the continuous ridge candidate group generation unit ensures that a single ridge candidate is not included in a plurality of continuous ridge candidate groups.

(Note 5) The fingerprint authentication system according to any one of Notes 1 to 4, wherein the determination unit determines that the abnormality exists in the image when a size of the overlap between the image regions corresponding to the continuous ridge candidate group equals or exceeds a predetermined size.

(Note 6) The fingerprint authentication system according to any one of Notes 1 to 5, wherein the abnormality corresponds to a case in which an image of a false finger formed by attaching a thin film to a surface of a finger is captured.

(Note 7) The fingerprint authentication system according to any one of Notes 1 to 6, wherein the ridge candidate extraction unit includes a first ridge candidate extraction unit that extracts ridge candidates determined to have a large amplitude, and a second ridge candidate extraction unit that extracts ridge candidates determined to have a small amplitude, the continuous ridge candidate group generation unit includes a first continuous ridge candidate group generation unit that generates a first continuous ridge candidate group by comparing the ridge candidates extracted by the first ridge candidate extraction unit, and a second continuous ridge candidate group generation unit that generates a second continuous ridge candidate group by comparing the ridge candidates extracted by the second ridge candidate extraction unit, and the determination unit determines that the abnormality exists in the image when overlap exists between an image region corresponding to the first continuous ridge candidate group and an image region corresponding to the second continuous ridge candidate group, or when overlap exists between the image regions corresponding to the second continuous ridge candidate group.

(Note 8) A fingerprint authentication method including the steps of: dividing a captured image of an authentication subject to be subjected to fingerprint authentication into a plurality of small regions; performing a frequency analysis on each of the small regions; extracting frequency components corresponding to ridge candidates in the small regions from frequency components obtained in the frequency analysis; comparing the ridge candidates between adjacent small regions, and when the ridge candidates satisfy a condition enabling the ridge candidates to be determined continuous, generating a continuous ridge candidate group including the ridge candidates; and determining that an abnormality exists in the image when overlap exists between the image regions corresponding to the continuous ridge candidate group.

(Note 9) A fingerprint authentication program for causing a computer to execute the steps according to Note 8.

This application claims priority based on Japanese Patent Application No. 2010-129059 filed on Jun. 4, 2010, the entire disclosure of which is incorporated herein.

The fingerprint authentication system, fingerprint authentication method, and fingerprint authentication program according to the present invention are suitable for improving the precision with which a false finger formed by attaching a transparent thin film to a surface of a finger is identified.

1 fingerprint authentication system
10 imaging unit
20 light source unit
30 control unit
31 image division unit
32 frequency analysis unit
33 ridge candidate extraction unit
33a first ridge candidate extraction unit
33b second ridge candidate extraction unit
34 continuous ridge candidate group generation unit
34a first continuous ridge candidate group generation unit
34b second continuous ridge candidate group generation unit
35 determination unit
40 output unit

What is claimed is:

1. A fingerprint authentication system comprising:
an image division unit that divides a captured image of an authentication subject to be subjected to fingerprint authentication into a plurality of small regions;
a frequency analysis unit that performs a frequency analysis on each of the small regions;
a ridge candidate extraction unit that extracts frequency components corresponding to ridge candidates in the small regions from frequency components obtained in the frequency analysis;
a continuous ridge candidate group generation unit that compares the ridge candidates between adjacent small regions, and when the ridge candidates satisfy a condition enabling the ridge candidates to be determined continuous, generates a continuous ridge candidate group including the ridge candidates; and
a determination unit that determines that an abnormality exists in the image when overlap exists between the image regions corresponding to the continuous ridge candidate group.

2. The fingerprint authentication system according to claim 1, wherein the frequency analysis unit performs a two-dimensional Fourier transform as the frequency analysis, and
the ridge candidate extraction unit extracts a group of local maximum points having origin symmetry when expressed on a frequency space by the two-dimensional Fourier transform as the frequency components corresponding to the ridge candidates.

3. The fingerprint authentication system according to claim 1, wherein the condition enabling the ridge candidates to be determined continuous is satisfied when a difference or a ratio between values of at least a part of a direction, a width, an amplitude, and a phase of the ridge candidates is smaller than a predetermined value.

4. The fingerprint authentication system according to claim 1, wherein the continuous ridge candidate group generation unit ensures that a single ridge candidate is not included in a plurality of continuous ridge candidate groups.

5. The fingerprint authentication system according to claim 1, wherein the determination unit determines that the abnormality exists in the image when a size of the overlap between the image regions corresponding to the continuous ridge candidate group equals or exceeds a predetermined size.

6. The fingerprint authentication system according to claim 1, wherein the abnormality corresponds to a case in which an image of a false finger formed by attaching a thin film to a surface of a finger is captured.

7. The fingerprint authentication system according to claim 1, wherein the ridge candidate extraction unit includes a first ridge candidate extraction unit that extracts ridge candidates determined to have a large amplitude, and a second ridge candidate extraction unit that extracts ridge candidates determined to have a small amplitude,
the continuous ridge candidate group generation unit includes a first continuous ridge candidate group generation unit that generates a first continuous ridge candidate group by comparing the ridge candidates extracted by the first ridge candidate extraction unit, and a second continuous ridge candidate group generation unit that generates a second continuous ridge candidate group by comparing the ridge candidates extracted by the second ridge candidate extraction unit, and
the determination unit determines that the abnormality exists in the image when overlap exists between an image region corresponding to the first continuous ridge candidate group and an image region corresponding to the second continuous ridge candidate group, or when overlap exists between the image regions corresponding to the second continuous ridge candidate group.

8. A fingerprint authentication method comprising:
dividing a captured image of an authentication subject, via an image division unit, to be subjected to fingerprint authentication into a plurality of small regions;
performing a frequency analysis, via a frequency analysis unit, on each of the small regions;
extracting frequency components, via a ridge candidate extraction unit, corresponding to ridge candidates in the small regions from frequency components obtained in the frequency analysis;
comparing the ridge candidates between adjacent small regions, via a continuous ridge candidate group generation unit, and when the ridge candidates satisfy a condition enabling the ridge candidates to be determined continuous, generating a continuous ridge candidate group including the ridge candidates; and
determining that an abnormality exists in the image, via a determination unit, when overlap exists between the image regions corresponding to the continuous ridge candidate group;
wherein one or more of the image division unit, the frequency analysis unit, the ridge candidate extraction unit, the continuous ridge candidate group generation unit, and the determination unit are implemented by a CPU.

9. A non-transitory computer readable medium storing a fingerprint authentication program for causing a computer to execute the steps according to claim 8.

* * * * *